(12) United States Patent
Wieters

(10) Patent No.: US 11,918,183 B2
(45) Date of Patent: Mar. 5, 2024

(54) ENDOSCOPE

(71) Applicant: OLYMPUS WINTER & IBE GMBH, Hamburg (DE)

(72) Inventor: Martin Wieters, Barsbuettel (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 231 days.

(21) Appl. No.: 17/430,354

(22) PCT Filed: Jan. 22, 2020

(86) PCT No.: PCT/EP2020/051471
§ 371 (c)(1),
(2) Date: Aug. 12, 2021

(87) PCT Pub. No.: WO2020/169297
PCT Pub. Date: Aug. 27, 2020

(65) Prior Publication Data
US 2022/0125290 A1  Apr. 28, 2022

(30) Foreign Application Priority Data

Feb. 21, 2019  (DE) .......................... 102019104489.8

(51) Int. Cl.
*A61B 1/00* (2006.01)
*A61B 1/12* (2006.01)
(52) U.S. Cl.
CPC ........ *A61B 1/0011* (2013.01); *A61B 1/00096* (2013.01); *A61B 1/00097* (2022.02); *A61B 1/127* (2013.01); *A61B 2562/0271* (2013.01)

(58) Field of Classification Search
CPC ... A61B 1/128; A61B 1/0011; A61B 1/00097; A61B 1/00096; A61B 1/127; A61B 2562/0271
See application file for complete search history.

(56) References Cited

U.S. PATENT DOCUMENTS

| | | | |
|---|---|---|---|
| 2003/0009162 A1* | 1/2003 | Messing | A61B 18/1492 606/41 |
| 2006/0271101 A1* | 11/2006 | Saadat | A61B 17/0401 606/205 |

(Continued)

FOREIGN PATENT DOCUMENTS

| | | |
|---|---|---|
| DE | 10 2008 031924 A1 | 1/2010 |
| DE | 20 2009 012 488 U1 | 4/2010 |

(Continued)

OTHER PUBLICATIONS

International Search Report dated Apr. 22, 2020 issued in PCT/EP2020/051471.

(Continued)

*Primary Examiner* — Timothy J Neal
(74) *Attorney, Agent, or Firm* — Scully, Scott, Murphy & Presser, P.C.

(57) ABSTRACT

An endoscope, including: at least one outer shaft tube, at least one inner shaft tube disposed within the at least one outer shaft tube; a window distally hermetically sealing one of the inner shaft tube or the outer shaft tube, a heater disposed proximate to the window between the at least one outer shaft tube and the at least one inner shaft tube, a temperature sensor disposed embedded in a potting compound proximate to the window, and an encasement filled with the potting compound, the encasement at least partially surrounding the temperature sensor.

16 Claims, 2 Drawing Sheets

(56) References Cited

U.S. PATENT DOCUMENTS

| | | | |
|---|---|---|---|
| 2008/0194915 A1* | 8/2008 | Blackhurst | G02B 23/2476 |
| | | | 126/400 |
| 2010/0010313 A1* | 1/2010 | Muckner | A61B 1/127 |
| | | | 600/169 |
| 2010/0016671 A1* | 1/2010 | Wieters | A61B 1/00097 |
| | | | 600/169 |
| 2010/0309553 A1* | 12/2010 | Nagamizu | A61B 1/127 |
| | | | 359/512 |
| 2014/0221743 A1 | 8/2014 | Sugiyama | |
| 2015/0272654 A1* | 10/2015 | Esch | A61B 18/1206 |
| | | | 606/34 |
| 2015/0313454 A1* | 11/2015 | Ide | A61B 1/127 |
| | | | 600/129 |
| 2017/0311789 A1* | 11/2017 | Mulcahey | A61B 1/126 |
| 2018/0192862 A1* | 7/2018 | Ide | G02B 23/24 |
| 2018/0228357 A1* | 8/2018 | Fujii | A61B 1/127 |
| 2020/0015750 A1* | 1/2020 | Pike | A61B 5/6848 |

FOREIGN PATENT DOCUMENTS

| | | |
|---|---|---|
| EP | 1 803 388 A2 | 7/2007 |
| EP | 2 957 213 A1 | 12/2015 |

OTHER PUBLICATIONS

Written Opinion dated Apr. 22, 2020 issued in PCT/EP2020/051471.
German Office Action dated Jan. 27, 2020 issued in DE 102019104489.9.

* cited by examiner

ENDOSCOPE

CROSS-REFERENCE TO RELATED APPLICATION

The present application is based upon and claims the benefit of priority from PCT/EP2020/051471 filed on Jan. 22, 2020, which claims priority to DE 10 2019 104 489.8 filed on Feb. 21, 2019, the entire contents of each of which is incorporated herein by reference.

BACKGROUND

Field

The present disclosure is related to an endoscope and more particularly to an endoscope comprising at least one outer shaft tube, at least one inner shaft tube disposed within the at least one outer shaft tube, a window distally hermetically sealing the inner shaft tube or the outer shaft tube, and a heating device disposed proximate to the window between the at least one outer shaft tube and the at least one inner shaft tube, the heating device comprising a temperature sensor which is disposed embedded in a potting material in the region of the window.

Prior Art

Endoscopes have long been used in medicine to examine or treat cavities in the body of a human or animal patient that are difficult to access. For this purpose, endoscopes usually comprise an elongated shaft with a main body attached to its proximal end, where the endoscope can be held. An objective lens is usually disposed at the distal end of the shaft, the image of which is transmitted to the proximal end via an optical or electronic image guide and is made available there by suitable means for viewing and/or evaluation. The distal end of the shaft is usually hermetically sealed by a window to prevent the ingress of contaminants or liquids.

The shaft of an endoscope may be flexible or rigid. Rigid shafts are composed of several shaft tubes disposed one inside the other; they are mainly used in urology, gynecology, and laparoscopy.

In laparoscopy, the endoscope is inserted through an artificial access into a patient's abdominal cavity, which is expanded with a gas. Moisture may condense on the window of the endoscope, especially at the beginning of a procedure where the endoscope is at a much lower temperature than the gas in the patient's abdominal cavity. This may sometimes obscure the attending physician's view to such an extent that he or she must interrupt the procedure and clean the window.

In order to avoid such condensation, endoscopes that have a heating device for the window have been known for some time. By means of the heating device, the window of the endoscope is heated to an elevated temperature even before it is inserted into the patient's abdominal cavity, so that the risk of condensation is significantly reduced.

However, there are very high requirements for the control of the heating device in such endoscopes, since, on the one hand, a sufficient temperature must be reached to avoid condensation and, on the other hand, regulatory limits for the surface temperature of medical instruments must be observed. The temperature of the window and adjacent sections of the shaft must therefore be maintained within a temperature range of, in some cases, a few Kelvin, for example between 37° C. and 40° C.

From DE 10 2008 031 924 A1, for example, an endoscope is known in which a heating foil is disposed between an outer shaft tube and an inner shaft tube, on which a temperature sensor is disposed.

In order to protect the temperature sensor from mechanical stresses during assembly and from thermal and chemical stresses during reprocessing of the endoscope, it has proved useful to embed the temperature sensor in a potting compound, e.g. in a drop of adhesive, also known as a "glob-top". However, it is difficult to control the exact shape of such a glob-top during manufacture. Variations in the thickness and/or shape of the glob-top may adversely affect the accuracy of the temperature measurement and thus the temperature control. Likewise, such variations may have a negative effect on the mechanical protection effect of the glob-top.

A distal end of an endoscope shaft 2 is shown in FIG. 2. The shaft comprises an outer shaft tube 10 and an inner shaft tube 11. Optical fibers 12 are placed between the outer shaft tube 10 and the inner shaft tube 11, which guide and radiate light to the distal end of the shaft 2 to illuminate the field of view of the endoscope 1.

The objective lens 4, which consists of a plurality of optical elements, and the electronic image converter 15 are disposed in the inner shaft tube 11. To protect the objective lens 4 and the image converter 15 from contaminants and liquids, the inner shaft tube 11 is hermetically sealed by a window 16.

A heating foil 20 is placed around the inner shaft tube 11, by means of which the distal end of the inner shaft tube 11 and the window 16 may be heated. Close to the window 16, a temperature sensor 21 is provided on the heating foil 20, which is surrounded by a drop 22 of a potting compound that protects the temperature sensor from damage.

The space between the outer shaft tube 10 and the inner shaft tube 11 is closed in the distal direction by a potting compound 25.

The exact dimensions of the droplet are difficult to control during manufacture, resulting in large variations in heat transfer between the inner shaft tube 11 and the temperature sensor.

SUMMARY

It is therefore an object to provide an endoscope which is improved with respect to the problems described.

Such object can be achieved by an endoscope comprising at least one outer shaft tube, at least one inner shaft tube disposed within the at least one outer shaft tube, a window distally hermetically sealing the inner shaft tube or the outer shaft tube, and a heating device disposed proximate to the window between the at least one outer shaft tube and the at least one inner shaft tube, the heating device comprising a temperature sensor which is disposed embedded in a potting compound in the region of the window, wherein the temperature sensor is at least partially surrounded by an encasement which is filled with the potting compound.

The encasement fixes the shape of the potting material with a low tolerance, so that a consistent accuracy of the temperature measurement and thus also of the temperature control may be achieved regardless of manufacturing tolerances.

In one possible embodiment of an endoscope, the temperature sensor may be disposed on a flexible printed circuit board. In this case, the correct placement of the temperature sensor in the vicinity of the window can be particularly easy and safe.

In one possible embodiment of an endoscope, the encasement may comprise a dome resting on the printed circuit board. The dome can completely define the shape of the potting compound.

In an embodiment of an endoscope, the encasement may comprise a ring resting on the printed circuit board. Due to the ring, the shape of the potting compound can be largely predetermined, while at the same time the insertion of the potting compound into the encasement can be significantly simplified.

The temperature sensor may comprise at least one thermistor. Alternatively, the temperature sensor can comprise two thermistors that are part of a bridge circuit.

In a possible implementation of an endoscope, the encasement may consist at least partially of a thermoplastic material. Such plastics are readily available and can be easily processed for manufacturing purposes, for example by injection molding.

The encasement may consist at least partially of a polyaryletherketone (PAEK), such as polyetheretherketone (PEEK), or of a polysulfone (PPSU). These plastics can be particularly temperature-stable and can therefore withstand the stresses of thermal processing of an endoscope.

In one possible embodiment of an endoscope, a thermosetting adhesive may be used as the potting material. Likewise, an adhesive that cures under UV radiation may be used.

In an embodiment of an endoscope, an adhesive may be used as a potting material which thermally cures under UV radiation after pre-curing. With such an adhesive, the rapid pre-curing can prevent the adhesive from unintentionally flowing out of the encasement, while optimum strength of the potting compound is achieved after the subsequent thermal curing. A possible adhesive for this purpose is, for example, EPO-TEK HYB 353ND from Epoxy Technology Inc, 14 Fortune Drive, Billerica, MA 01821, USA.

In a further embodiment of an endoscope, the printed circuit board may comprise geometric reference marks for alignment of the encasement. This can make it particularly easy and reliable to accurately position the encasement on the printed circuit board as part of an automated manufacturing process.

BRIEF DESCRIPTION OF THE DRAWINGS

The embodiments are explained in more detail below with reference to a number of exemplary embodiments, the embodiments being intended merely to aid understanding without limiting the scope of the following claims, in which:

DETAILED DESCRIPTION

Figure 1:
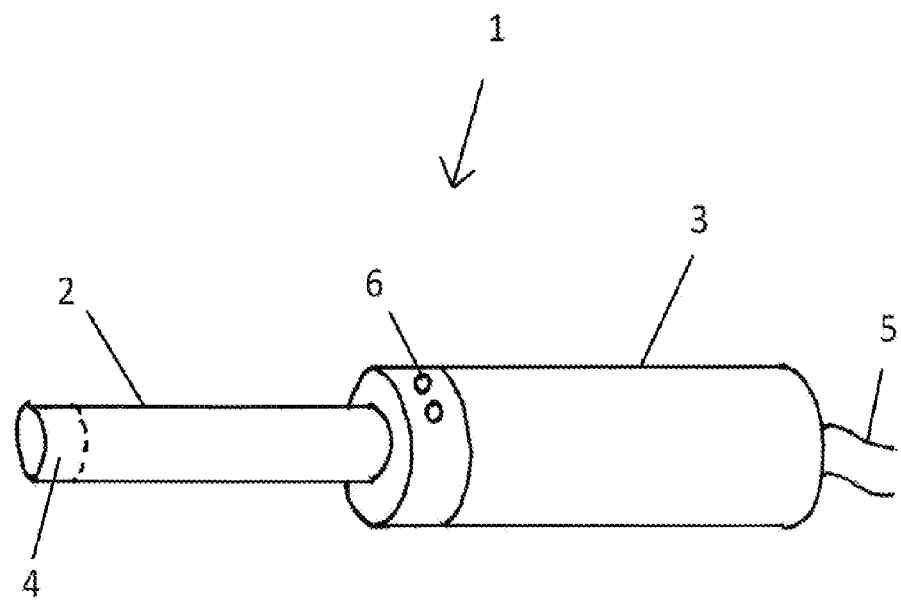
FIG. 1 illustrates an endoscope.

FIG. 1 shows an endoscope 1 with an elongated shaft 2 and a main body 3. An objective lens 4 is disposed in the distal end of the shaft 2. The image from the objective lens is converted into electrical video signals by an electronic image converter, not shown, and transmitted to the main body 3. From the main body 3, the video signals are output via a cable 5, if necessary, after electronic preprocessing.

Operating switches 6 are provided in the distal area of the main body, via which functions of the endoscope 1 or connected devices can be controlled. Signals from the operating switches 6 are also routed via the cable 5.

Figure 2:
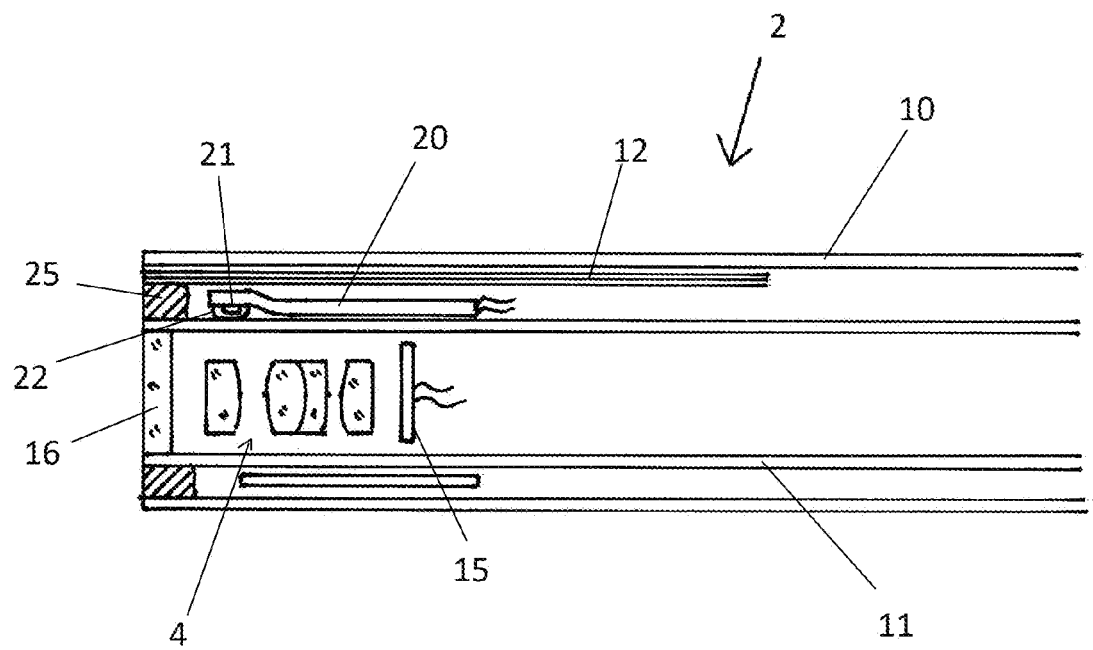
FIG. 2 illustrates the distal end of the shaft of an endoscope according to the prior art.
Figure 3A:
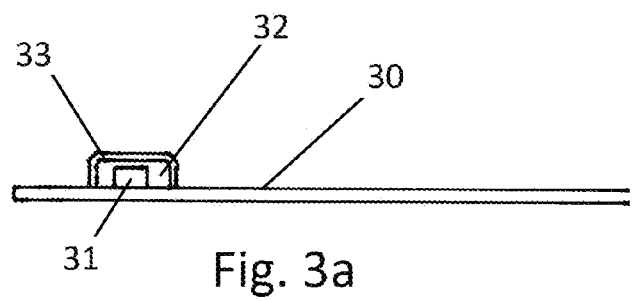
FIGS. 3a and 3b illustrate sections of a heating foil.
Figure 3B:
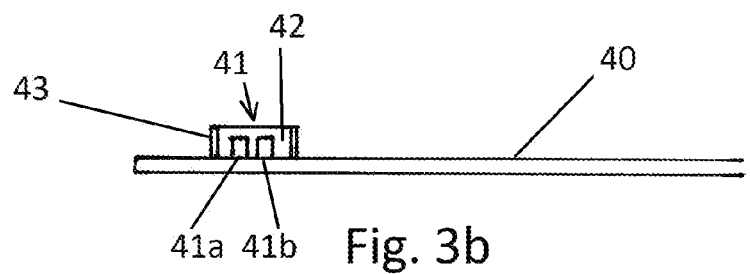

FIGS. 3a and 3b show heating foils which may be used in place of the heating foil 20 of FIG. 2.

FIG. 3a shows a section of a heating foil 30 with a temperature sensor 31, which in turn is embedded in a potting compound 32. To ensure a reproducible shape of the potting compound 32 and thus also a reproducible heat transfer to the temperature sensor 31, the potting compound 32 is embedded in an encasement in the form of a dome 33 placed on the heating foil 31.

FIG. 3b shows a section of a heating foil 40 with a temperature sensor 41. In the example shown, the temperature sensor 41 consists of two thermistors 41a, 41b. Here, too, the potting compound 42 is surrounded by an encasement, which is configured in the form of a ring 43. Here, after fastening the ring 43, the potting compound 42 can be introduced into it particularly easily and then cured, for example, by means of a UV lamp not shown. For this purpose, a UV-curing adhesive can be used as the potting compound 42. Alternatively, a thermosetting adhesive or a hybrid adhesive may be used which, after being pre-cured by UV radiation during which the viscosity of the adhesive increases, is completely thermally cured by the application of heat.

The dome 33 and the ring 43 may be made of thermoplastic material. Because of the high temperatures that occur during the reprocessing of endoscopes, temperature-resistant plastics such as PAEK, PEEK or PPSU can be used.

Figure 4:
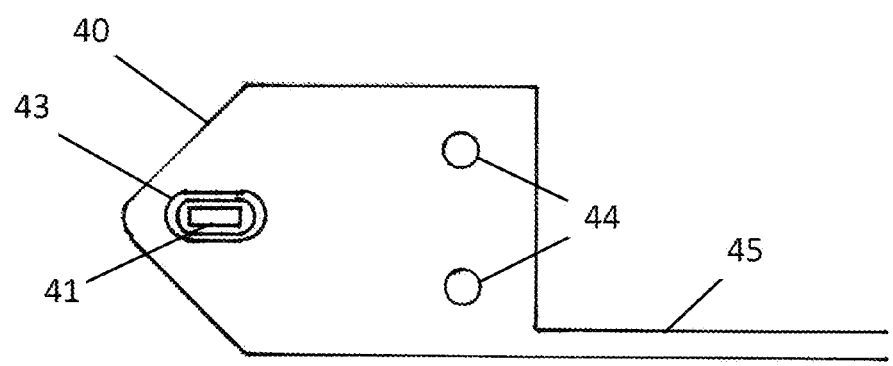
FIG. 4 illustrates a heating foil.

FIG. 4 shows a top view of the heating foil 40, with the temperature sensor 41 and the ring 43 visible. In order to place the ring 43 correctly during the production of the heating foil 40 in a semi- or fully-automated process, reference markings 44 in the form of through-holes are provided in the heating foil 40, by means of which the heating foil 30 can be precisely positioned in a device.

An extension 45 of the heating foil 40 is provided for contacting purpose at the proximal end of the shaft 2.

The described embodiments are simplified in many respects to facilitate understanding thereof. For example, the shaft of an endoscope may have more than the two shaft tubes shown. Likewise, the objective lens may have a much more complicated structure than shown herein.

In one embodiment of an endoscope not shown, the outer shaft tube 10 may be surrounded by a further shaft tube, with the window 16 hermetically sealing the outer shaft tube 10 in place of the inner shaft tube 11, and the optical fibers 12 being disposed between the outer shaft tube 10 and the further shaft tube.

The features of the individual embodiments shown may be combined with each other. For example, in an embodiment of the heating foil according to FIG. 3b, a one-piece temperature sensor, such as a single thermistor, may be used. Similarly, in an embodiment according to FIG. 3a, the temperature sensor 31 may comprise two thermistors. Also, the heating foil shown in FIG. 3a may also have reference markings and/or an extension for contacting.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An endoscope, comprising:
at least one outer shaft tube,
at least one inner shaft tube disposed within the at least one outer shaft tube;
a window distally hermetically sealing one of the inner shaft tube or the outer shaft tube,
a heater disposed proximate to the window between the at least one outer shaft tube and the at least one inner shaft tube, the heater comprising a heater foil disposed around an outer shape of the at least one inner shaft tube,
a temperature sensor disposed on the heater foil and embedded in a potting compound, the temperature sensor being positioned proximate to the window, and
an encasement filled with the potting compound, the encasement surrounding the temperature sensor.

2. The endoscope according to claim 1, wherein the encasement comprises a dome resting on the heater foil.

3. The endoscope according to claim 1, wherein the encasement comprises a ring resting on the heater foil.

4. The endoscope according to claim 1, wherein the temperature sensor comprises at least one thermistor.

5. The endoscope according to claim 4, wherein the at least one thermistor comprises two thermistors.

6. The endoscope according to claim 1, wherein the encasement is at least partially formed of a thermoplastic material.

7. The endoscope according to claim 6, wherein the thermoplastic material is polyaryletherketone.

8. The endoscope according to claim 7, wherein the polyaryletherketone is polyetheretherketone.

9. The endoscope according to claim 1, wherein the potting compound comprises a thermosetting adhesive.

10. The endoscope according to claim 1, wherein the potting compound comprises an adhesive that cures under UV radiation.

11. The endoscope according to claim 1, wherein the potting compound comprises a hybrid adhesive which thermally cures under UV radiation after pre-curing.

12. The endoscope according to claim 1, wherein the heating foil comprises geometric reference marks for alignment of the encasement.

13. An endoscope, comprising:
at least one outer shaft tube,
at least one inner shaft tube disposed within the at least one outer shaft tube;
a window distally hermetically sealing one of the inner shaft tube or the outer shaft tube,
a heater disposed proximate to the window between the at least one outer shaft tube and the at least one inner shaft tube, the heater comprising a heater foil disposed around an outer shape of the at least one inner shaft tube,
on the heater foil and embedded in a potting compound, the temperature sensor being positioned proximate to the window, and
an encasement filled with the potting compound, the encasement having an inner surface and an outer surface defining a wall, the wall at least partially surrounding the temperature sensor.

14. The endoscope according to claim 13, wherein the wall defines a dome.

15. The endoscope according to claim 13, wherein the wall defines a ring.

16. An endoscope, comprising:
at least one outer shaft tube,
at least one inner shaft tube disposed within the at least one outer shaft tube;
a window distally hermetically sealing one of the inner shaft tube or the outer shaft tube,
a heater disposed proximate to the window between the at least one outer shaft tube and the at least one inner shaft tube,
a temperature sensor disposed embedded in a potting compound proximate to the window, and
an encasement filled with the potting compound, the encasement at least partially surrounding the temperature sensor,
wherein the heater is a heater foil and the temperature sensor is disposed on the heater foil; and
the heater foil comprises geometric reference marks for alignment of the encasement.

* * * * *